United States Patent
Hermle

(10) Patent No.: US 10,856,991 B2
(45) Date of Patent: Dec. 8, 2020

(54) ARTIFICIAL JOINT IMPLANT AND HIP JOINT ENDOPROSTHESIS

(71) Applicant: Aesculap AG, Tuttlingen (DE)

(72) Inventor: Thomas Hermle, Rottweil (DE)

(73) Assignee: Aesculap AG, Tuttlingen (DE)

( * ) Notice: Subject to any disclaimer, the term of this patent is extended or adjusted under 35 U.S.C. 154(b) by 0 days.

(21) Appl. No.: 15/992,596

(22) Filed: May 30, 2018

(65) Prior Publication Data

US 2018/0271664 A1    Sep. 27, 2018

Related U.S. Application Data

(63) Continuation of application No. PCT/EP2016/080563, filed on Dec. 12, 2016.

(30) Foreign Application Priority Data

Dec. 11, 2015 (DE) .......... 10 2015 121 658

(51) Int. Cl.
*A61F 2/36* (2006.01)
*A61F 2/30* (2006.01)

(52) U.S. Cl.
CPC .............. *A61F 2/3609* (2013.01); *A61F 2/30* (2013.01); *A61F 2/36* (2013.01); *A61F 2/3662* (2013.01); *A61F 2002/365* (2013.01); *A61F 2002/3652* (2013.01); *A61F 2002/3674* (2013.01)

(58) Field of Classification Search
CPC .. A61F 2002/3674; A61F 2/3672; A61F 2/36; A61F 2/3601; A61F 2002/3605; A61F 2/3609; A61F 2002/3625; A61F 2002/3652; A61F 2/3662; A61F 2/3676; A61F 2/4014; A61F 2002/4044; A61F 2/4059; A61F 2002/30317; A61F 2002/30329; A61F 2002/30369; A61F 2002/30364; A61F 2220/0025; A61F 2220/0033

See application file for complete search history.

(56) References Cited

U.S. PATENT DOCUMENTS

| | | | |
|---|---|---|---|
| 5,002,581 A | 3/1991 | Paxson et al. | |
| 5,876,459 A * | 3/1999 | Powell | A61F 2/3609 623/23.15 |
| 6,090,146 A * | 7/2000 | Rozow, III | A61F 2/30721 411/290 |

(Continued)

FOREIGN PATENT DOCUMENTS

| | | |
|---|---|---|
| CA | 2775785 | 3/2011 |
| CN | 102573705 | 7/2012 |

(Continued)

*Primary Examiner* — Alvin J Stewart
(74) *Attorney, Agent, or Firm* — Lipsitz & McAllister, LLC

(57) ABSTRACT

The invention relates to an artificial joint implant, having a first implant part, a second implant part, and at least one fixing element for fixing the first and the second implant part to each other in an at least one of non-positive- and positive-locking manner in a connecting position, wherein the at least one fixing element and the first implant part are moveably coupled to each other in a non-detachable manner, in such a way that the at least one fixing element is detachable from the first implant part only by destroying the at least one fixing element or the first implant part.

24 Claims, 4 Drawing Sheets

(56) References Cited

U.S. PATENT DOCUMENTS

Figure 3:
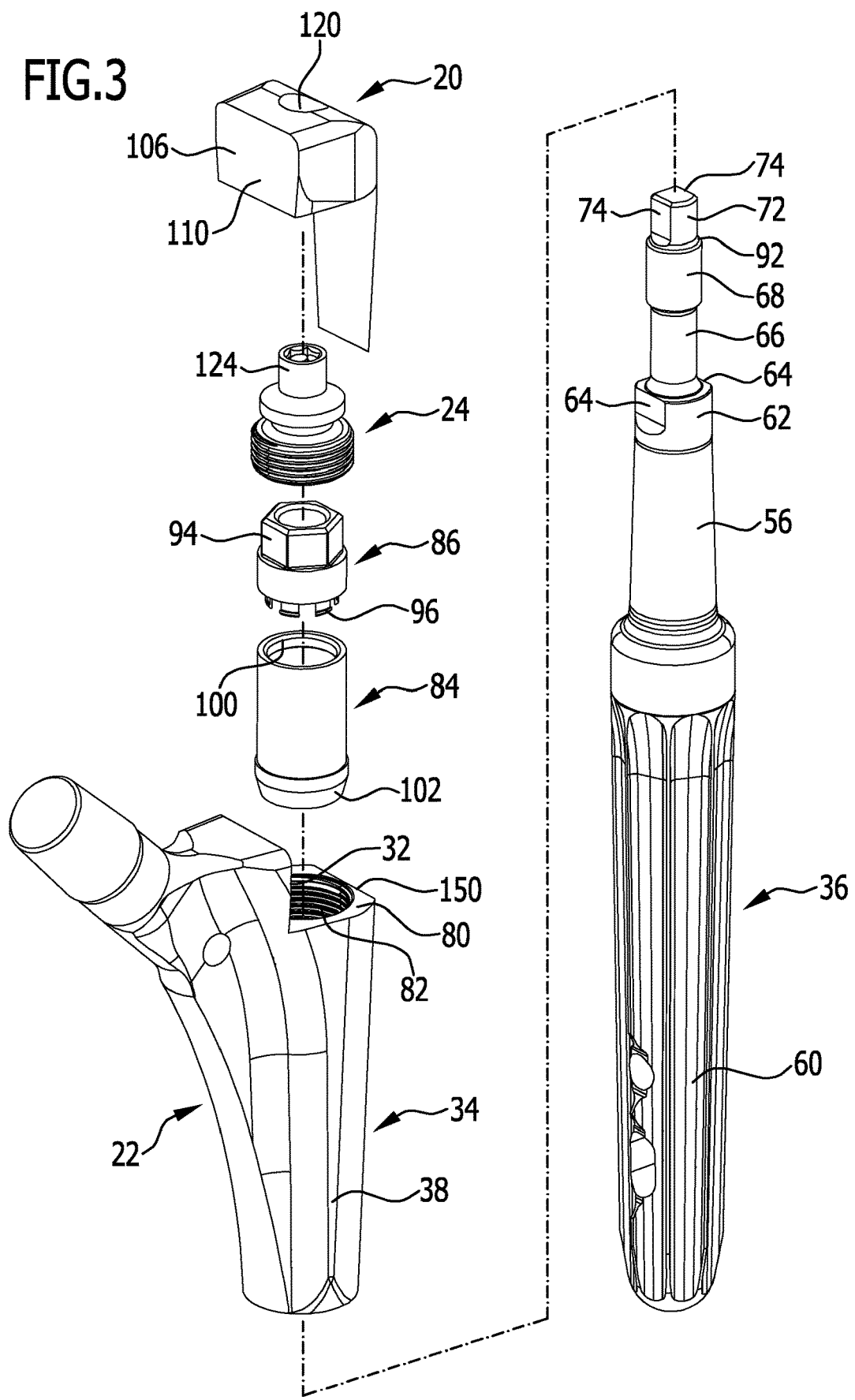

| | | | |
|---|---|---|---|
| 6,299,648 B1* | 10/2001 | Doubler | A61F 2/36 623/22.42 |
| 8,333,807 B2* | 12/2012 | Smith | A61F 2/468 623/20.35 |
| 8,556,975 B2 | 10/2013 | Ciupik et al. | |
| 9,138,326 B2 | 9/2015 | Siedler et al. | |
| 2002/0058999 A1* | 5/2002 | Dwyer | A61F 2/30734 623/22.42 |
| 2003/0074078 A1* | 4/2003 | Doubler | A61F 2/36 623/22.42 |
| 2003/0204269 A1* | 10/2003 | Gerbec | A61F 2/30734 623/23.47 |
| 2004/0073315 A1* | 4/2004 | Justin | A61F 2/389 623/20.15 |
| 2004/0122440 A1* | 6/2004 | Daniels | A61F 2/36 606/102 |
| 2004/0122524 A1* | 6/2004 | Hunter | A61F 2/30767 623/22.18 |
| 2004/0122525 A1* | 6/2004 | Daniels | A61F 2/36 623/22.42 |
| 2005/0004679 A1* | 1/2005 | Sederholm | A61F 2/30734 623/22.42 |
| 2006/0105296 A1* | 5/2006 | Linder | A61C 8/005 433/173 |
| 2007/0123908 A1* | 5/2007 | Jones | A61B 17/164 606/102 |
| 2008/0125867 A1* | 5/2008 | McCleary | A61F 2/4684 623/22.4 |
| 2009/0123890 A1* | 5/2009 | Purga | A61C 8/0018 433/174 |
| 2011/0077738 A1 | 3/2011 | Ciupik et al. | |
| 2012/0000063 A1* | 1/2012 | Leisinger | A61F 2/3609 29/525.11 |
| 2013/0110244 A1 | 5/2013 | Siedler et al. | |
| 2015/0018961 A1* | 1/2015 | Huddle | A61F 2/4684 623/22.4 |
| 2015/0081021 A1 | 3/2015 | Ciupik | |
| 2016/0175116 A1* | 6/2016 | Bader | A61F 2/4657 606/86 R |
| 2019/0231540 A1* | 8/2019 | Kim | A61F 2/30 |
| 2019/0247153 A1* | 8/2019 | Zipprich | A61C 8/0048 |

FOREIGN PATENT DOCUMENTS

| | | |
|---|---|---|
| CN | 104185458 | 12/2014 |
| DE | 4320086 | 12/1994 |
| DE | 102005052699 | 2/2007 |
| DE | 102008030260 | 12/2009 |
| DE | 202011103010 | 12/2012 |
| EP | 0428303 | 5/1991 |
| FR | 2660857 | 10/1991 |

* cited by examiner

FIG.1
FIG.2
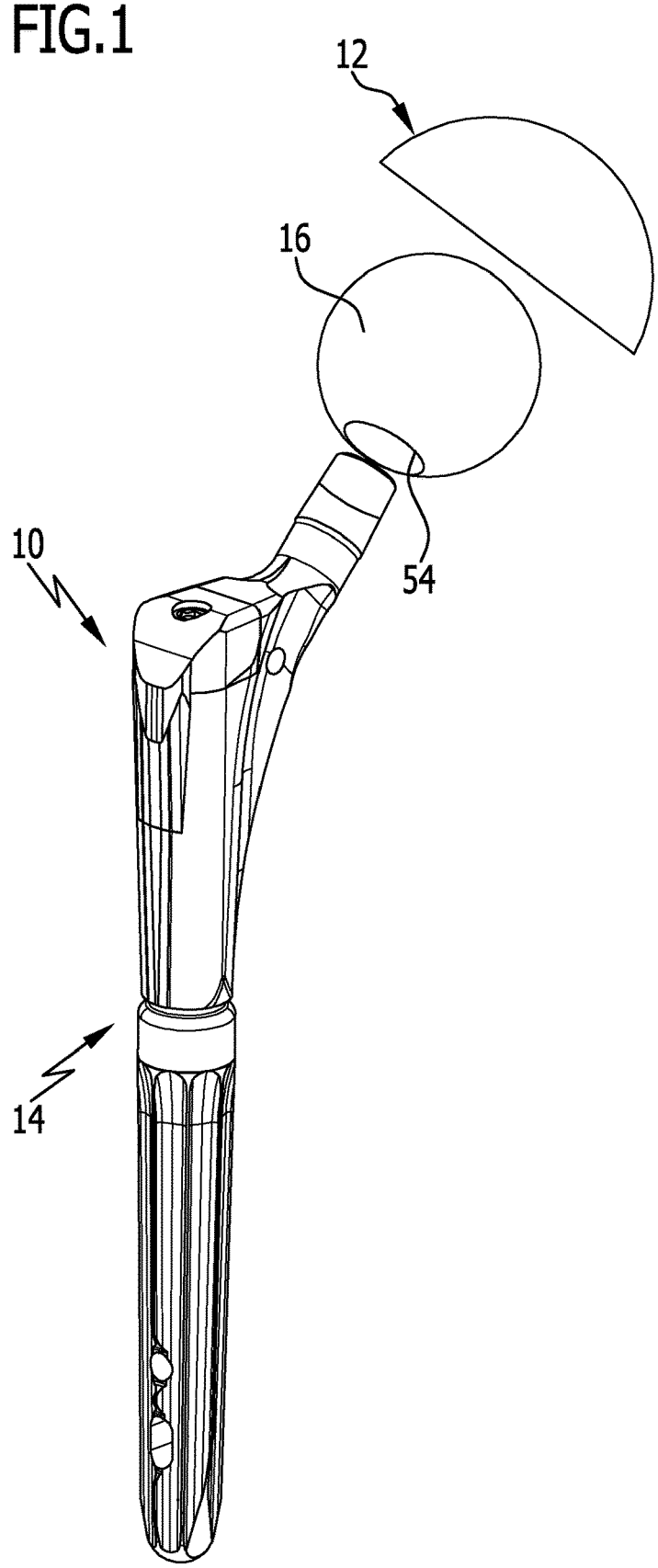
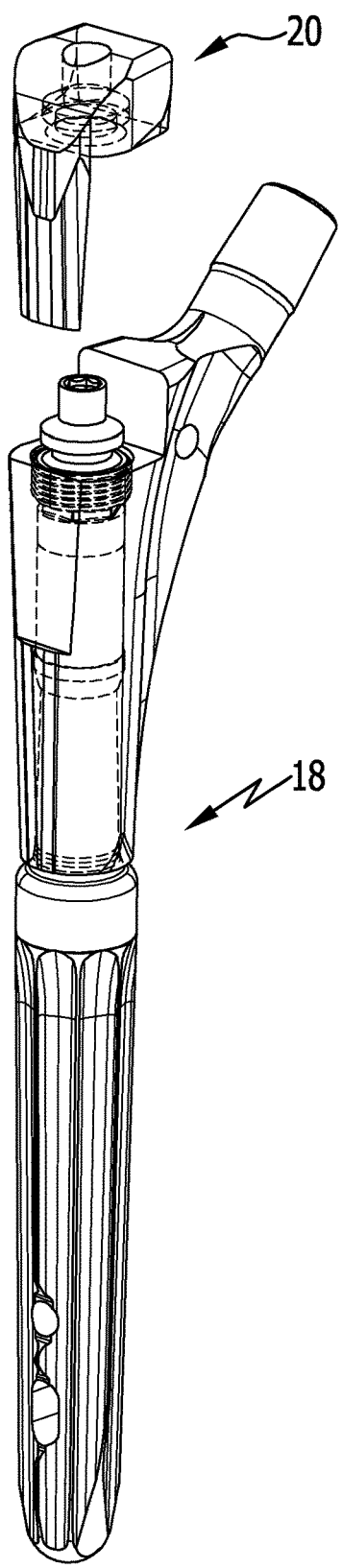

ARTIFICIAL JOINT IMPLANT AND HIP JOINT ENDOPROSTHESIS

This application is a continuation of international application number PCT/EP2016/080563 filed on Dec. 12, 2016 and claims the benefit of German application number 10 2015 121 658.2 filed on Dec. 11, 2015, which are incorporated herein by reference in their entirety and for all purposes.

FIELD OF THE INVENTION

The invention relates to artificial joint implants generally, and more specifically to an artificial joint implant having a first implant part, a second implant part, and at least one fixing element for fixing the first and the second implant part to each other in a non-positive- and/or positive-locking manner in a connecting position.

Further, the present invention relates to hip joint endoprostheses generally, and more specifically to a hip joint endoprosthesis comprising a joint socket and a hip shank which bears a joint head interacting with the joint socket or which is coupleable to such a joint head.

BACKGROUND OF THE INVENTION

Artificial joint implants of the kind described at the outset are known in a variety of ways. For example, it may hereby be concerning components of hip joint endoprostheses or knee joint endoprostheses.

In particular in the case of modular prosthesis systems, it is common to fix first and second implant parts to each other in a connecting position using at least one fixing element. For example, shoulders are formed on hip joint shanks separately from the shank itself, and are connected to the shank after the insertion of the shank into a cavity of the femur, for example by way of screwing. Typically at least one fixing element is used for this purpose.

In the known modular systems, connecting the first and second implant part to the at least one fixing element is laborious, however.

SUMMARY OF THE INVENTION

In a first aspect of the invention, an artificial joint implant has a first implant part, a second implant part, and at least one fixing element for fixing the first and the second implant part to each other in a non-positive- and/or positive-locking manner in a connecting position. The at least one fixing element and the first implant part are moveably coupled to each other in a non-detachable manner, in such a way that the at least one fixing element is detachable from the first implant part only by destroying the at least one fixing element or the first implant part, In a second aspect of the invention, a hip joint endoprosthesis comprises a joint socket and a hip shank, which bears a joint head interacting with a joint socket or that is coupleable to such a joint head. The hip shank is configured in the form of an artificial joint implant. Said joint implant has a first implant part, a second implant part, and at least one fixing element for fixing the first and the second implant part to each other in a non-positive- and/or positive-locking manner in a connecting position. The at least one fixing element and the first implant part are moveably coupled to each other in a non-detachable manner, in such a way that the at least one fixing element is detachable from the first implant part only by destroying the at least one fixing element or the first implant part.

BRIEF DESCRIPTION OF THE DRAWING FIGURES

Figure 4:
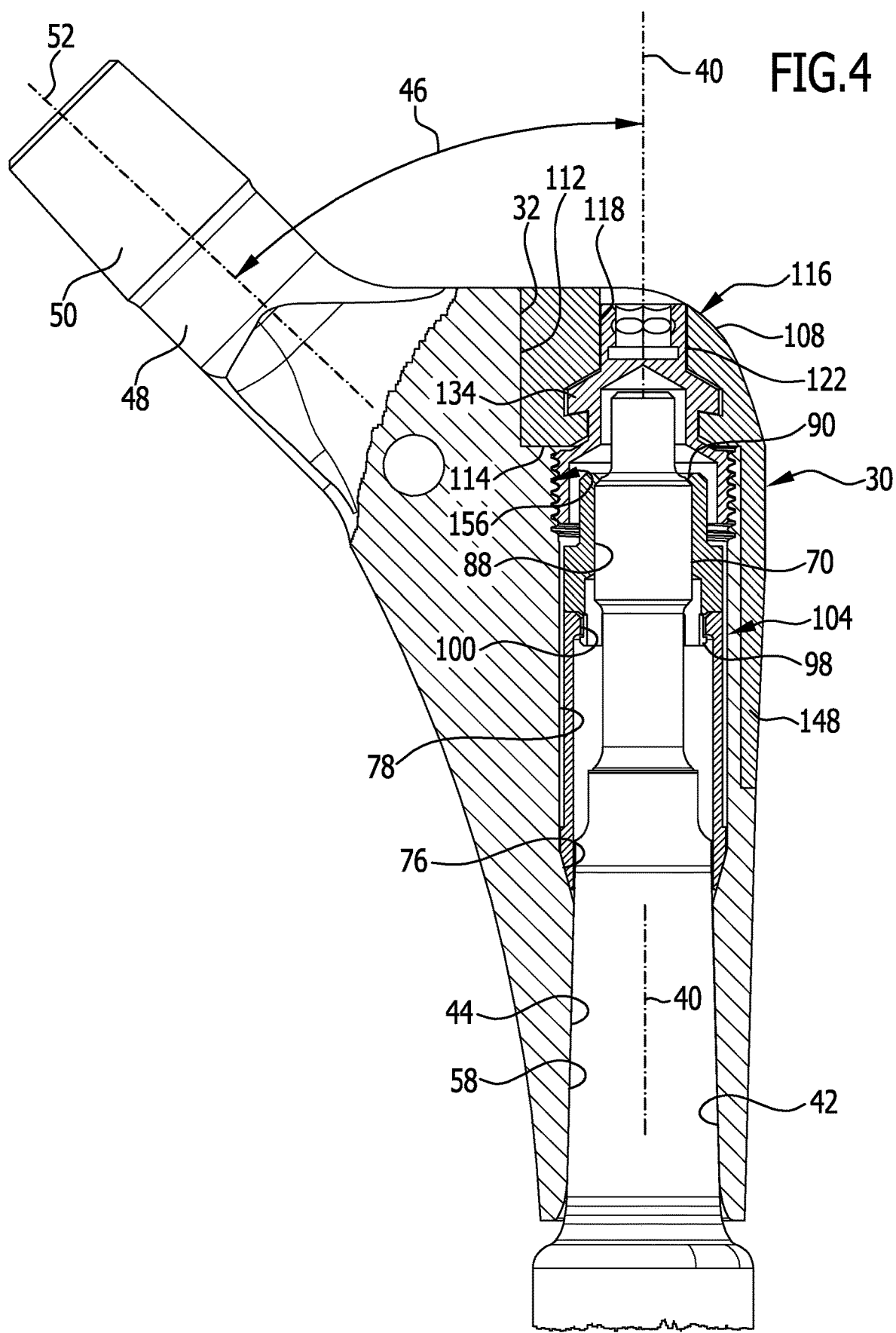
Figure 5:
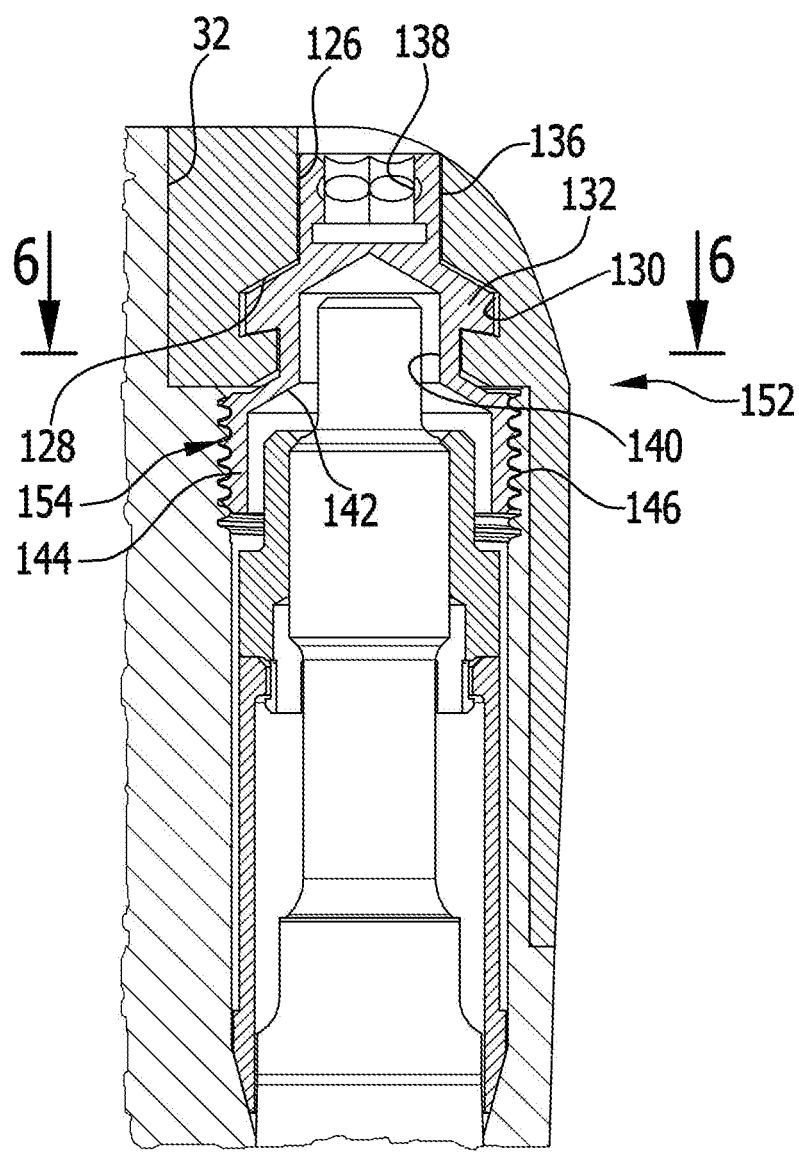
Figure 6:
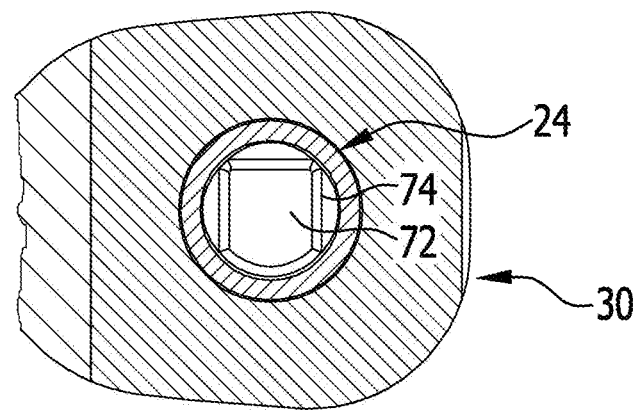

The foregoing summary and the following description may be better understood in conjunction with the drawing figures, of which:

FIG. 1: shows a perspective view of a hip joint endoprosthesis, configured as a revision prosthesis, having an artificial joint implant in the form of a hip shank;

FIG. 2: shows a partial broken depiction of the artificial joint implant from FIG. 1 having a removed closure element;

FIG. 3: shows a perspective exploded depiction of the artificial joint implant from FIG. 1;

FIG. 4: shows a partial longitudinal sectional view of the artificial joint implant from FIG. 1;

FIG. 5: shows an enlarged section of the longitudinal sectional view from FIG. 4; and FIG. 6: shows a sectional view along line 6-6 in FIG. 5.

DETAILED DESCRIPTION

Although the invention is illustrated and described herein with reference to specific embodiments, the invention is not intended to be limited to the details shown. Rather, various modifications may be made in the details within the scope and range of equivalents of the claims and without departing from the invention.

The present invention relates to an artificial joint implant, having a first implant part, a second implant part, and at least one fixing element for fixing the first and the second implant part to each other in a non-positive- and/or positive-locking manner in a connecting position, wherein the at least one fixing element and the first implant part are moveably coupled to each other in a non-detachable manner, in such a way that the at least one fixing element is detachable from the first implant part only by destroying the at least one fixing element or the first implant part, The solution proposed in accordance with the invention enables a simpler implantation of the joint implant. The at least one fixing element is moveably coupled to the first implant part, but is not detachable therefrom. As a result, it cannot get lost. In particular if the at least one fixing element is configured in the form of a screw or a nut, which are rather small in comparison to the size of the implant parts to be connected to each other, it is advantageous if the at least one fixing element cannot unintendedly detach from the first implant part and get lost. In addition, the implant parts may be formed having a space-saving design. Also a positioning of multiple parts of the joint implant is operatively simplified. In addition, an operation time may be reduced as a positive consequence. As a result of the non-detachable coupling of the at least one fixing element and the implant part, the number of the parts of the joint implant which are to be handled by a surgeon may also be reduced.

The at least one fixing element and the first implant part are preferably coupled to each other so as to be twistable and/or displaceable relative to each other. For example, a nut or a screw may form a first fixing element which is held on the first implant part so as to be displaceable and/or twistable relative to the first implant part. For example, the screw or the nut may thus be twisted and/or displaced relative to the first implant part, such that it may be screwed to a corresponding second fixing element, for example an internally threaded bore or a threaded bolt, in order to fix the first and the second implant part to each other in the connecting position.

In accordance with a further embodiment of the invention, the joint implant may comprise a coupling device for moveably coupling the at least one fixing element and the first implant part in a coupling position, which coupling device has cooperative first and second coupling elements which are engaged with each other in the coupling position, which coupling elements are arranged or formed, on the one hand, on the first implant part and, on the other hand, on the at least one fixing element. Using a coupling device of that kind, fixing elements and implant parts may be brought into engagement with each other in a simple manner, such that they are held together so as to be moveable relative to each other, but still non-detachably. Non-detachably held together means here, again, that a detachment of the parts from each other is only possible by destroying one or both parts.

It is advantageous if the first coupling element is configured in the form of a coupling recess, and that the second coupling element is configured in the form of a coupling projection corresponding to the coupling recess. For moveably coupling the first implant part and the at least one fixing element, the first and second coupling elements are engaged in particular in the described manner.

The joint implant may be constructed in a particularly simple and compact manner if a perforation is formed on the first implant part, and if the perforation forms the coupling recess. For example, it may hereby concern a bore in which the at least one fixing element or a part thereof engages in the coupling position.

It is favorable if an undercut is arranged or formed on the first and/or on the second coupling element, and if an undercut projection engaging in the undercut is arranged or formed on the respective other coupling element. By way of the undercut interacting with the undercut projection, a non-detachable connection of the first and the second coupling element in the coupling position may be achieved in a simple manner, wherein the coupling elements may be held together so as to still be moveable relative to each other.

The production of the joint implant is made particularly simple if the undercut is configured in the form of an annular groove and if the undercut projection is configured in the form of an annular projection corresponding to the annular groove. The annular projection itself does not necessarily need to be closed in itself. There may also be multiple annular projections provided pointing in the direction toward a longitudinal axis or away therefrom, which may ensure a secure coupling of the first and second coupling elements to each other in the coupling position.

It is advantageous if the annular groove is formed open pointing in the direction toward a longitudinal axis of the coupling device or pointing away therefrom, and if the annular projection is arranged or formed protruding pointing away from the longitudinal axis or toward it. Coupling elements interengaging in that way prevent in particular a detachment of the at least one fixing element and the first implant part from each other in a direction parallel to the longitudinal axis.

The first and/or the second coupling element preferably defines the longitudinal axis. For example, the first and/or the second coupling element may be formed rotationally symmetrically and define the longitudinal axis with an axis of symmetry.

It is favorable if the first and/or the second coupling element are configured rotationally symmetrically or substantially rotationally symmetrically to the longitudinal axis. The coupling elements and thus the coupling device overall may therefore be produced in a simple manner.

In order to have to provide only a minimal number of parts for the artificial joint implant, it is favorable if the first and the second coupling element are each integrally formed. In addition, a particularly stable coupling between the at least one fixing element and the first implant part may thus be achieved, which coupling may only be released by destroying the at least one fixing element or the first implant part.

It is advantageous if the first and/or the second coupling element are formed by way of an additive manufacturing method. First and/or second coupling elements produced in that way may be formed in a simple manner and in one working operation by way of such an additive manufacturing method, which may also be referred to as a generative manufacturing method. In addition, an undercut and one or more undercut projections engaging therein may also be formed in one working operation. A complex mounting, in order to non-detachably connect the at least one fixing element and the first implant part to each other, is thus not necessary.

The joint implant may be produced in a particularly simple manner if the first and/or the second coupling element are formed by way of a 3D-printing method or by way of selective laser sintering. In particular, the at least one fixing element and/or the first implant part may also be formed altogether by way of the described additive manufacturing method.

It is favorable if the at least one fixing element and/or the first implant part and/or the second implant part is integrally formed. In this way, only a minimal number of parts need to be connected to each other upon implantation of the hip implant. This simplifies the handling and helps to reduce an operation time.

In accordance with another preferred embodiment of the invention, the joint implant may comprise a connecting device for connecting the at least one fixing element and the second implant part to each other in a connecting position in a non-positive- and/or positive-locking manner. By way of said connecting device, the first and the second implant part may then be fixed to each other in a non-positive- and/or positive-locking manner.

It is advantageous if the connecting device comprises first and second connecting elements which are arranged or formed, on the one hand, on the at least one fixing element and, on the other hand, on the second implant part, and which are engaged in a non-positive- and/or positive locking manner in the connecting position, and which are disengaged in a separating position in which the at least one fixing element and the second implant part are separated from each other. A connecting device configured in that way enables in particular in a simple manner a non-positive- and/or positive-locking connection between the at least one fixing element and the second implant part, and thus also between the first and the second implant part.

The joint implant may be constructed in a simple manner if the first connecting element is configured in the form of a connecting projection, and the second connecting element in the form of a connecting receiver or vice versa. A connecting projection—formed for example on the at least one fixing element—and a corresponding connecting receiver may be brought into engagement with each other in a simple manner.

The joint implant may be produced in a simple manner if the connecting receiver is configured on the second implant part in the form of a perforation or in the form of a blind hole. Alternatively, the second connecting element may also be configured in the form of a projecting pin or bolt.

The connecting elements may be brought into engagement with each other in a simple manner if the first and second connecting elements are configured to be latchable and/or screwable to each other. A latching together between the connecting elements enables in particular a tool-free connection between the at least one fixing element and the second implant part. A screwable design has in particular the advantage that the at least one fixing element and the second implant part may also be separated from each other again in a simple manner as needed.

It is favorable if the first connecting element has an externally threaded section and the second connecting element an internally threaded section corresponding to the externally threaded section. Connecting elements configured in that way enable screwing the at least one fixing element and the second implant part to each other in a simple manner.

In order to further improve a handling of the joint implant during the implantation, it is favorable if a tool element receiver is arranged or formed on the coupling element of the at least one fixing element for being brought into engagement with a tool, in particular a screwing-in tool, for connecting the at least one fixing element and the second implant part to each other. The tool element receiver enables in particular bringing the at least one fixing element into engagement with the second implant part in a non-positive- and/or positive-locking manner using a corresponding tool. For example, the tool element receiver may be configured in the form of an internal multi-round.

It is advantageous if the first implant part and/or the second implant part and/or the at least one fixing element are produced from a biocompatible metal and/or plastics material. Selecting materials of that kind has in particular the advantage that the risk of rejections by the body of the patient is minimized.

The artificial joint implant is preferably configured in the form of a prosthesis shank of a hip joint endoprosthesis. Alternatively, the joint implant may also be configured in the form of a tibial part or a femoral part of a knee joint endoprosthesis, or in the form of a prosthesis shank of a shoulder joint prosthesis. In principle, the joint implant may fit to any endoprosthesis if it is modularly constructed and comprises at least two implant parts to be connected to each other.

It is favorable if the prosthesis shank comprises a shank part for insertion into a bone cavity of a femur and a closure element for a shank part opening of the shank part, and if the shank part defines the second implant part and the closure element defines the first implant part. The closure element may in particular be configured in the form of a shoulder of a revision prosthesis which is connected to the shank part only after insertion of the shank part into the bone cavity of the femur. The at least one fixing element may in particular be configured as a rotatable screw bolt or a nut which is rotatably held on the closure element and which may be screwed to the shank part in a non-positive and/or positive-locking manner.

Favorably, the shank part is modularly constructed and has a neck part and a shank, which are engaged in a non-positive- and/or positive-locking manner in the implantation position. The modular construction enables providing individual lengths of the shank in order to be able to optimally treat a patient.

The invention also relates to a hip joint endoprosthesis comprising a joint socket and a hip shank, which bears a joint head interacting with a joint socket or that is coupleable to such a joint head, wherein the hip shank is configured in the form of an artificial joint implant, said joint implant having a first implant part, a second implant part, and at least one fixing element for fixing the first and the second implant part to each other in a non-positive- and/or positive-locking manner in a connecting position, wherein the at least one fixing element and the first implant part are moveably coupled to each other in a non-detachable manner, in such a way that the at least one fixing element is detachable from the first implant part only by destroying the at least one fixing element or the first implant part.

Such a hip joint endoprosthesis has in particular the advantages described in conjunction with preferred embodiments of artificial joint implants.

A hip joint endoprosthesis 10 is schematically depicted for example in FIG. 1. It comprises in particular a joint socket 12 and a hip shank 14, which is coupleable to a joint head 16 cooperating with the joint socket 12.

The hip shank 14 is configured in the form of an artificial joint implant 18 and comprises a first implant part 20, a second implant part 22, and a fixing element 24 for fixing the first and the second implant part to each other in a non-positive- and/or positive-locking manner in a connecting position, as is schematically depicted for example in FIGS. 1, 4, 5, and 6.

The hip shank 14 forms a prosthesis shank 26 of the hip joint endoprosthesis 10. It comprises a shank part 28 for insertion into a bone cavity of a femur. The shank part 28 comprises in particular the second implant part 22.

The prosthesis shank further comprises a closure element 30 for a shank part opening 32 which is configured in the form of a cutout on a neck part 34 of the modularly constructed shank part 28.

The shank part 28 further comprises a shank 36 which is engaged with or connected to the neck part 34 in a non-positive- and/or positive-locking manner in an implantation position. The implantation position is schematically depicted for example in FIGS. 1, 2, 4, and 5.

The neck part 34 comprises a shank receiver section 38 which has a shank receiver 42 that is in the form of a perforation 44, defines a longitudinal axis 40, and is formed rotationally symmetrically with respect to the longitudinal axis 40.

Protruding from the shank receiver section 38 at an angle 46 of about 45 degrees is a neck section 48 which has a free end configured in the form of a connecting cone 50. The neck section 48 defines a neck longitudinal axis 52, which encloses the angle 46 with the longitudinal axis 40.

Corresponding to the connecting cone 50, a cone receiver conically tapering in the direction toward a center of the joint head 16 is formed on the joint head 16. The joint head 16 and the neck section 48 may thus be connected by way of a press fit connection.

The shank 36 has a cone section 56 protruding into the shank receiver 42, which corresponds to an internal cone 58 in the region of the shank receiver 42, such that a press fit connection may here too be formed. A shank section 60 projecting distally out of the shank receiver 42 in the implantation position is optionally provided with a profiling, in order to enable an optimized ingrowth into the cavity of the femur.

For securing the shank 36 in the shank receiver 42, a first tool section 62 is formed on the shank proximally of the cone section 56, having two flat portions 64 oriented parallel to each other and to the longitudinal axis. A cylindrical section 66 reduced in diameter connects proximally to the first tool section 62. Somewhat shorter than the section 66 is a cylindrical bolt section 68 connecting proximally thereon, which is provided with an external threading 70. A proximal end of the shank 36 forms a second tool section 72, which also has two flat portions 74 running parallel to each other and parallel to the longitudinal axis 40.

The shank receiver 42 widens somewhat in internal diameter proximally of the internal cone 58 while forming a conical shoulder 76, and is configured in the form of a cylindrical bore. Commencing from a proximal end 80 of the neck part, which delimits the shank part opening 32, a short internally threaded section 82 is formed in the bore 78.

A clamping sleeve 84 and a nut 86 serve to connect the shank 36 to the neck part 34. The nut 86 has an internal threading 88 which corresponds to the external threading 70 of the bolt section 68. Further, a proximal end of the nut 86 which connects to the internal threading 88 is formed projecting somewhat in the direction toward the longitudinal axis 40 in the manner of a flange 90. The flange 90 cooperates with an annular stop face 92 in the transition region between the first bolt section 68 and the second tool section 72.

The nut 86 has a proximal end configured in the form of an external hexagon 94. A distal end of the nut 86 is configured in the form of a sleeve section having latching elements 96 pointing in distal direction, which bear latch noses 98 pointing away from the longitudinal axis 40 that engage behind an annular flange 100 in the clamping sleeve 84 that points in the direction toward the longitudinal axis 40. The annular flange 100 is formed directly on the proximal end of the clamping sleeve 84.

The clamping sleeve 84 ends distally in an externally formed conical clamping face 102 that is formed corresponding to the shoulder 76 and is supported thereon when the shank 36 is connected to the neck part 34.

The latching elements 96 and the annular flange 100 form a latching connecting device 104 for connecting the clamping sleeve 84 and the nut 86 in a latching manner. The latching connecting device 104 makes it possible in particular to twist the nut 86 relative to the clamping sleeve 84 about the longitudinal axis 40. The clamping sleeve 84 may then abut on the shoulder 76 in a non-rotatable manner and then, by twisting the nut 86 relative to the bolt section 68, the shank 36 may be drawn as far as possible into the shank receiver 42 and, respectively, the press fit connection formed between the cone section 56 and the internal cone 58 may be secured.

The first implant part 20 substantially forms a shank shoulder 106 that has a rounded outer surface 108 and a planar contact face 110 against a contact face 112 of the shank part opening 32 which corresponds to said contact face 110 and faces parallel to the longitudinal axis 40 and toward said contact face 110.

An underside of the shank shoulder 106 also forms a contact face 114 that runs perpendicularly to the longitudinal axis 40 and is intended for abutment on the end 80.

A particularity of the joint implant 18 is in particular that the fixing element 24 and the first implant part 20 are moveably coupled with each other in a non-detachable manner, in such a way that the fixing element 24 is detachable from the first implant part only by destroying it or by destroying the first implant part 20.

In the embodiment of the joint implant 18 exemplarily depicted in the Figures, the fixing element 24 and the first implant part 20 are coupled to each other so as to be twistable relative to each other about the longitudinal axis 40 and to be minimally displaceable relative to each other in the direction of the longitudinal axis 40.

A coupling device 116, which comprises a first coupling element 118 in the form of a coupling recess 120, serves to couple the fixing element 24 and the first implant part 20. A second coupling element 122 is configured on the fixing element 24 in the form of a coupling projection 124 formed correspondingly to the coupling recess 120.

The coupling recess 120 is defined by a perforation 126 of the first implant part 20 coaxially to the longitudinal axis 40.

In order to moveably hold the first implant part 20 and the fixing element 24 together in a non-detachable manner, an undercut 128 is configured on the first implant part 20 in the region of the perforation 126 in the form of an annular groove 130 open in the direction toward the longitudinal axis 40.

An undercut projection 132 corresponding to the undercut 128 and engaging therein is configured on the fixing element 24 in the form of an annular projection 134 pointing away from the longitudinal axis 40 in radial direction.

Proximally of the annular projection 134 on the fixing element 24 is formed a cylindrical end section 136 which has a tool element receiver 138 that is open pointing in proximal direction, for example in the form of an internal polygon or an internal multi-round.

The fixing element 24 further has a blind hole 140 which is open pointing in distal direction and into which the second tool section 72 dips, without contacting the fixing element 24.

The blind hole 140 widens in internal diameter in a short transition region 142 and forms a screw sleeve 144 having an external threading 146 and defining a distal end of the fixing element 24. The external threading 146 is formed correspondingly to the internally threaded section 82. The screw sleeve 144 having the external threading 146 forms a first connecting element 154 of a connecting device, designated as a whole with the reference numeral 152, for connecting the fixing element 24 to the second implant part in a non-positive- and/or positive-locking manner in a connecting position. The internally threaded section 82, which is formed on the shank receiver 42 and into which the screw sleeve 144 is screwable, forms a second connecting element 156 of the connecting device 152.

On the shank shoulder 106 is further formed a plate-like projection 148 which points in distal direction, protrudes from the contact face 114, and which abuts on a planar side face 150 of the neck part 34. The side face 150 points away from the longitudinal axis 40 and runs parallel to the contact face 112.

By way of the undercut 128 and the undercut projection 132, the fixing element 24 and the first implant part 20 are detachable from each other only by destroying either the fixing element 24 and/or the first implant part 20 in such a way that the undercut projection 132 no longer engages in the undercut 128.

In order to be able to configure the fixing element 24 and the first implant part 20 in the described manner, they are formed in one production step by way of a generative manufacturing method. For example, they may both be formed from a plastics material and be produced by way of a 3D-printing method. The first implant part 20 and the fixing element 24 are thereby formed in layers from a material that is solidifiable by electromagnetic radiation, for example, in particular a liquid resin.

Alternatively, the production may also take place by way of selective laser sintering. In this manufacturing method, metal powder is hardened in layers by way of melting via exposure to a laser beam at high intensity, and subsequent cooling off thereof. The fixing element 24 and the first implant part 20 may thus also be formed from metallic materials.

The first implant part 20 may be connected to the second implant part 22 by simply screwing on. For this purpose, a screwing-in tool not depicted may be engaged in the tool element receiver 138 on the fixing element 24 and the fixing element may be rotated about the longitudinal axis 40 for screwing in the external threading 146 and the shank sleeve 144 into the internally threaded section 82 on the shank receiver 42. The undercut projection 132 then holds the closure element 30 in the shank part opening 32.

The separation of the shank shoulder 106 from the neck part 34 may advantageously take place for multiple reasons. For one, various operation techniques may be better supported by way of the modular construction of the shank part 28. In particular, a more gentle entry with the neck part 34 upon insertion thereof into the body of the patient is made possible. The insertion of the shank shoulder 106 for filling out the shank part opening 32 may then take place after the insertion of the shank 35 into the cavity of the femur of the patient.

The particular shaping of the shank shoulder 106 may take place for different purposes. In particular a structure which grows in better may thus be selected. For example, surfaces of the first implant part 20 and the second implant part 22 may be selected differently. Further, the shank shoulder 106 may offer an additional support, in particular in order to fix soft tissues thereon. Further, the shank shoulder 106 may also be optimized to that effect, in order to better fix bone fragments.

The joint implant 18 described in conjunction with the FIGS. 1 to 6 may also be formed as part of other endoprostheses for insertion into the human body. In principle, such a joint implant 18 may be provided anywhere where a modular construction thereof is required and the fixing element 24 is moveably coupled in the described way to the first implant part 20 or to the second implant part 22 in a non-detachable manner to avoid small parts that may get lost.

REFERENCE NUMERAL LIST 10 hip joint endoprosthesis
12 acetabular
14 hip shank
16 joint head
18 joint implant
20 first implant part
22 second implant part
24 fixing element
26 prosthesis shank
28 shank part
30 closure element
32 shank part opening
34 neck part
36 shank
38 shank receiver section
40 longitudinal axis
42 shank receiver
44 perforation
46 angle
48 neck section
50 connecting cone
52 neck longitudinal axis
54 cone receiver
56 cone section
58 internal cone
60 shank section
62 first tool section
64 flat portion
66 section
68 bolt section
70 external threading
72 second tool section
74 flat portion
76 shoulder
78 bore
80 end
82 internally threaded section
84 clamping sleeve
86 nut
88 internal threading
90 flange
92 stop face
94 external hexagon
96 latching element
98 latch nose
100 annular flange
102 clamping face
104 latching connecting device
106 shank shoulder
108 outer face
110 contact face
112 contact face
114 contact face
116 coupling device
118 first coupling element
120 coupling recess
122 second coupling element
124 coupling projection
126 perforation
128 undercut
130 annular groove
132 undercut projection
134 annular projection
136 end section
138 tool element receiver
140 blind hole
142 transition region
144 screw sleeve
146 external threading
148 projection
150 side face
152 connecting device
154 first connecting element
156 second connecting element

What is claimed is:
1. Artificial joint implant, comprising:
a first implant part,
a second implant part, and
at least one fixing element for fixing the first and the second implant part to each other in an at least one of non-positive- and positive-locking manner in a connecting position,
wherein:
the at least one fixing element and the first implant part are moveably coupled to each other in a non-detachable manner, in such a way that the at least one fixing element is detachable from the first implant part only by destroying the at least one fixing element or the first implant part, the at least one fixing element and the first implant part are coupled to each other so as to be at least one of twistable and displaceable relative to each other, and the at least one fixing element is of a monolithic construction.

2. Artificial joint implant in accordance with claim 1, further comprising a coupling device for moveably coupling the at least one fixing element and the first implant part in a coupling position, the coupling device comprising cooperative first and second coupling elements which are engaged with each other in the coupling position, which coupling elements are arranged or formed, on the one hand, on the first implant part and, on the other hand, on the at least one fixing element.

3. Artificial joint implant in accordance with claim 2, wherein the first coupling element is configured in the form of a coupling recess, and wherein the second coupling element is configured in the form of a coupling projection corresponding to the coupling recess.

4. Artificial joint implant in accordance with claim 3, wherein a perforation is formed on the first implant part, and wherein the perforation forms the coupling recess.

5. Artificial joint implant in accordance with claim 2, wherein at least one undercut is arranged or formed on at least one of the first and the second coupling element, and wherein an undercut projection engaging in the undercut is arranged or formed on the respective other coupling element.

6. Artificial joint implant in accordance with claim 5, wherein the undercut is configured in the form of an annular groove, and wherein the undercut projection is configured in the form of an annular projection corresponding to the annular groove.

7. Artificial joint implant in accordance with claim 6, wherein the annular groove is formed open with a perimetral wall thereof pointing in a direction toward a longitudinal axis of the coupling device or pointing away therefrom, and wherein the annular projection is arranged or formed protruding pointing away from the longitudinal axis or pointing toward it.

8. Artificial joint implant in accordance with claim 7, wherein at least one of the first and the second coupling element defines the longitudinal axis.

9. Artificial joint implant in accordance with claim 8, wherein at least one of the first and the second coupling element is formed rotationally symmetrically or substantially rotationally symmetrically to the longitudinal axis.

10. Artificial joint implant in accordance with claim 2, wherein the first and the second coupling element at least one of:
a) are each integrally formed,
and
b) are formed by way of an additive manufacturing method,
and
c) are formed by way of a 3D-printing method or by way of selective laser sintering.

11. Artificial joint implant in accordance with claim 2, wherein:
a) a tool element receiver is arranged or formed on the coupling element of the at least one fixing element for being brought into engagement with a tool for connecting the at least one fixing element and the second implant part to each other,
or
b) a tool element receiver is arranged or formed on the coupling element of the at least one fixing element for being brought into engagement with a screwing-in tool for connecting the at least one fixing element and the second implant part to each other.

12. Artificial joint implant in accordance with claim 1, wherein at least one of the first implant part and the second implant part is integrally formed.

13. Artificial joint implant in accordance with claim 1, further comprising a connecting device for connecting the at least one fixing element and the second implant part to each other in an at least one of non-positive- and positive-locking manner in a connecting position.

14. Artificial joint implant in accordance with claim 13, wherein the connecting device comprises first and second connecting elements which are arranged or formed, on the one hand, on the at least one fixing element and, on the other hand, on the second implant part, and which are engaged in an at least one of non-positive- and positive-locking manner in the connecting position, and which are disengaged in a separating position in which the at least one fixing element and the second implant part are separated from each other.

15. Artificial joint implant in accordance with claim 14, wherein:
a) the first connecting element is configured in the form of a connecting projection, and the second connecting element in the form of a connecting receiver or vice versa,
or
b) the first connecting element is configured in the form of a connecting projection, and the second connecting element in the form of a connecting receiver or vice versa,
wherein the connecting receiver is configured on the second implant part in the form of a perforation or in the form of a blind hole.

16. Artificial joint implant in accordance with claim 14, wherein at least one of:
a) the first and second connecting elements are configured to be at least one of latchable and screwable to each other,
and
b) the first connecting element has an externally threaded section, and in that the second connecting element has an internally threaded section corresponding to the externally threaded section.

17. Artificial joint implant in accordance with claim 1, wherein at least one of:
a) at least one of the first implant part and the second implant part and the at least one fixing element are produced from at least one of a biocompatible metal and plastics material,
and
b) wherein the joint implant is configured in the form of a prosthesis shank of a hip joint endoprosthesis.

18. Artificial joint implant in accordance with claim 17, wherein:
a) the prosthesis shank comprises a shank part for insertion into a bone cavity of a femur and a closure element for a shank part opening of the shank part, and
the shank part defines the second implant part and the closure element the first implant part,
or
b) the prosthesis shank comprises a shank part for insertion into a bone cavity of a femur and a closure element for a shank part opening of the shank part, and
the shank part defines the second implant part and the closure element the first implant part, wherein the shank part is modularly constructed and has a neck part and a shank, which are engaged in an at least one of non-positive- and positive-locking manner in the implantation position.

19. Hip joint endoprosthesis comprising:
a joint socket and a hip shank, which bears a joint head interacting with a joint socket or that is coupleable to such a joint head,
wherein:
the hip shank is configured in the form of an artificial joint implant, said joint implant comprising a first implant part, a second implant part, and at least one fixing element for fixing the first and the second implant part to each other in an at least one of non-positive- and positive-locking manner in a connecting position, and
the at least one fixing element and the first implant part are moveably coupled to each other in a non-detachable manner, in such a way that the at least one fixing element is detachable from the first implant part only by destroying the at least one fixing element or the first implant part.

20. Artificial joint implant, comprising:
a first implant part,
a second implant part,
at least one fixing element for fixing the first and the second implant part to each other in an at least one of non-positive- and positive-locking manner in a connecting position,
the at least one fixing element and the first implant part being moveably coupled to each other in a non-detachable manner, in such a way that the at least one fixing element is detachable from the first implant part only by destroying the at least one fixing element or the first implant part,
a coupling device for moveably coupling the at least one fixing element and the first implant part in a coupling position, the coupling device comprising cooperative first and second coupling elements which are engaged with each other in the coupling position, which coupling elements are arranged or formed, on the one hand, on the first implant part and, on the other hand, on the at least one fixing element, and
the at least one fixing element is of a monolithic construction.

21. Artificial joint implant, comprising:
a first implant part,
a second implant part, and
at least one fixing element for fixing the first and the second implant part to each other in an at least one of non-positive- and positive-locking manner in a connecting position,
wherein:
the at least one fixing element and the first implant part are moveably coupled to each other in a non-detachable manner, in such a way that the at least one fixing element is detachable from the first implant part only by destroying the at least one fixing element or the first implant part, and
at least one of:
a) at least one of the first implant part and the second implant part and the at least one fixing element are produced from at least one of a biocompatible metal and plastics material, and
b) wherein the joint implant is configured in the form of a prosthesis shank of a hip joint endoprosthesis.

22. Artificial joint implant in accordance with claim 21, wherein the at least one fixing element and the first implant part are coupled to each other so as to be at least one of twistable and displaceable relative to each other.

23. Artificial joint implant, comprising:
a first implant part,
a second implant part,
at least one fixing element for fixing the first and the second implant part to each other in an at least one of non-positive- and positive-locking manner in a connecting position, and
a coupling device for moveably coupling the at least one fixing element and the first implant part in a coupling position, the coupling device comprising cooperative first and second coupling elements which are engaged with each other in the coupling position, which coupling elements are arranged or formed, on the one hand, on the first implant part and, on the other hand, on the at least one fixing element,
wherein:
the at least one fixing element and the first implant part are moveably coupled to each other in a non-detachable manner, in such a way that the at least one fixing element is detachable from the first implant part only by destroying the at least one fixing element or the first implant part,
the at least one fixing element and the first implant part are coupled to each other so as to be at least one of twistable and displaceable relative to each other,
at least one undercut is arranged or formed on at least one of the first and the second coupling element,
an undercut projection engaging in the undercut is arranged or formed on the respective other coupling element,
the undercut is configured in the form of an annular groove, and wherein the undercut projection is configured in the form of an annular projection corresponding to the annular groove, and
the annular groove is formed open with a perimetral wall thereof pointing in a direction toward a longitudinal axis of the coupling device or pointing away therefrom, and wherein the annular projection is arranged or formed protruding pointing away from the longitudinal axis or pointing toward it.

24. Artificial joint implant, comprising:
a first implant part,
a second implant part,
at least one fixing element for fixing the first and the second implant part to each other in an at least one of non-positive- and positive-locking manner in a connecting position, and
a connecting device for connecting the at least one fixing element and the second implant part to each other in an at least one of non-positive- and positive-locking manner in a connecting position,
wherein:
the at least one fixing element and the first implant part are moveably coupled to each other in a non-detachable manner, in such a way that the at least one fixing element is detachable from the first implant part only by destroying the at least one fixing element or the first implant part,
the at least one fixing element and the first implant part are coupled to each other so as to be at least one of twistable and displaceable relative to each other, and
the connecting device comprises first and second connecting elements which are arranged or formed, on the one hand, on the at least one fixing element and, on the other hand, on the second implant part, and which are engaged in an at least one of non-positive- and positive-locking manner in the connecting position, and which are disengaged in a separating position in which the at least one fixing element and the second implant part are separated from each other.

\* \* \* \* \*